United States Patent [19]

Hukasawa

[11] Patent Number: 5,112,480
[45] Date of Patent: * May 12, 1992

[54] BLOOD RESERVOIR

[75] Inventor: Hiromichi Hukasawa, Fuji, Japan

[73] Assignee: Terumo Kabushiki Kaisha, Tokyo, Japan

[ * ] Notice: The portion of the term of this patent subsequent to Mar. 19, 2008 has been disclaimed.

[21] Appl. No.: 457,786

[22] PCT Filed: Jul. 6, 1988

[86] PCT No.: PCT/JP88/00681

§ 371 Date: Mar. 2, 1990

§ 102(e) Date: Mar. 2, 1990

[87] PCT Pub. No.: WO89/00056

PCT Pub. Date: Dec. 1, 1989

[30] Foreign Application Priority Data

Jul. 7, 1987 [JP] Japan ................................ 62-167768

[51] Int. Cl.$^5$ ............................................ B01D 19/00
[52] U.S. Cl. .................................. 210/188; 210/257.2; 210/489; 210/496; 55/159; 55/178; 422/45
[58] Field of Search ................... 210/188, 257.1, 257.2, 210/496, 489; 55/159, 178; 422/45

[56] References Cited

U.S. PATENT DOCUMENTS

| 4,061,031 | 12/1977 | Grimsrud | 210/188 |
| 4,073,622 | 2/1978 | Luppi | 55/178 |
| 4,568,367 | 2/1986 | Gremel et al. | 210/188 |
| 4,620,965 | 11/1986 | Fukusawa et al. | 210/321.8 |
| 4,704,203 | 11/1987 | Reed | 210/188 |
| 4,743,371 | 5/1988 | Servas et al. | 210/188 |
| 5,000,764 | 5/1991 | Oshiyama et al. | 210/188 |

5,026,525 6/1991 Katsura .................................. 422/45

FOREIGN PATENT DOCUMENTS

| 249048 | 3/1963 | Australia . |
| 42955 | 6/1979 | Australia . |
| 54513/80 | 7/1980 | Australia . |
| 26601 | 10/1984 | Australia . |
| 0049461 | 4/1982 | European Pat. Off. . |
| 0145158 | 6/1985 | European Pat. Off. . |
| 0206638 | 5/1988 | European Pat. Off. . |
| 59-57661 | 4/1984 | Japan . |
| 60-81546 | 6/1985 | Japan . |
| 61-45770 | 3/1986 | Japan . |
| 62-258671 | 11/1987 | Japan . |
| 1016869 | 1/1966 | Switzerland . |
| 416950 | 1/1967 | Switzerland . |

Primary Examiner—W. Gary Jones
Attorney, Agent, or Firm—Frishauf, Holtz, Goodman & Woodward

[57] ABSTRACT

A blood reservoir serves to remove air bubbles from blood and maintain a desired amount of blood in an extracorporeal blood circulation circuit. The blood reservoir has a blood inlet chamber having blood inlet ports, a blood storage chamber having a blood outlet port, and a blood debubblizer disposed between the blood inlet chamber and the blood storage chamber and extending the full width across the blood passage defined by the blood inlet chamber. A rib is held against the side of the debubblizer closer to the blood storage chamber and extends the full width across the blood passage, the rib having a certain height. Blood introduced into the blood reservoir is forced by the rib to stay in the debubblizer, during which time air bubbles are reliably removed from the blood by the debubblizer.

4 Claims, 5 Drawing Sheets (PRIOR ART)

BLOOD RESERVOIR

TECHNICAL FIELD

The present invention relates to a blood reservoir for use with an artificial lung, the blood reservoir including a debubblizer for reliably removing air bubbles from blood stored in the blood reservoir.

BACKGROUND ART

When a surgical operation is effected on the chest of a patient, an extracorporeal blood circulation circuit including an artificial lung is used in recent years in bypassing relation to the lung of the patient, and carbon dioxide is removed from the blood of the patient and fresh oxygen is added to the blood by the artificial lung.

The extracorporeal blood circulation circuit includes a blood reservoir for temporarily storing the blood so that air bubbles produced during the circulation of the blood will be removed from the blood, or for supplying stored blood to make up for a reduction in the rate of circulation of the blood. Blood reservoirs now in use in the art are roughly classified into a soft bag type which is made of a soft material, and a hard shell type which is made of a hard material. The soft bag reservoir is advantageous in that it has no blood-air interface, but disadvantageous in that it cannot hold a large amount of blood and cannot give an exact indication of how much blood is stored therein.

The hard shell reservoir can store a large amount of blood and allows the user to know the exact amount of blood stored therein. Other advantages of the hard shell reservoir are that it can easily be united with an artificial lung, thus permitting an extracorporeal blood circulation circuit to be simplified, and also the blood can easily be debubblized when the extracorporeal blood circulation circuit is set up and primed. Japanese Laid-Open Patent Publication No. 59(1984)-57661, for example, proposes a hard shell blood reservoir combined with an artificial lung.

It is very important that a hard shell blood reservoir be capable of reliably removing air bubbles which have been introduced into the blood through a blood extracting tube. If the blood containing air bubbles were returned to the patient, then the patient would suffer from the danger of embolism. The hard shell blood reservoir therefore has a debubblizer for removing air bubbles from the stored blood.

One known hard shell blood reservoir with a debubblizer, which is combined with an artificial lung, is a blood reservoir LPM 50 (manufactured by Baxter Travenol Laboratories, Inc.) as shown in FIG. 1 of the accompanying drawings. The blood reservoir, denoted at 2, has a blood debubblizer 8 disposed in a blood inlet chamber 6 near a blood inlet port 4 and held in contact with the bottom of the blood inlet chamber 6. Blood B which has been introduced from an artificial lung 10 through a heat exchanger 12 into the blood reservoir 2 flows into a blood storage chamber 14 without being subjected to a large resistance by the debubblizer 8. Since the blood B is not kept in effective contact with the debubblizer 8, the debubblizer 8 fails to debubblize the blood B effectively. Air bubbles, particularly small air bubbles, contained in the blood B therefore tend to be carried into the blood storage chamber 14 by the flow of the blood B.

DISCLOSURE OF THE INVENTION

In view of the aforesaid drawbacks of the conventional blood reservoirs, it is an object of the present invention to provide a blood reservoir which includes a debubblizer that can effectively be kept in contact with introduced blood for a greater debubblizing capability, so that air bubbles contained in the blood can effectively be removed.

To achieve the above object, there is provided in accordance with the present invention a blood reservoir comprising a blood inlet chamber having a blood inlet port, a blood storage chamber communicating with the blood inlet chamber and having a blood outlet port in a lower end which is positioned downwardly of the blood inlet chamber, and a blood debubblizer extending fully across a blood passage of the blood inlet chamber which leads to the blood storage chamber, characterized by a rib held against the side of the debubblizer closer to the blood storage chamber and extending fully across the blood passage, the rib projecting a predetermined distance upwardly from the bottom of the blood inlet chamber.

The rib has a height ranging from 1 mm to 50 mm.

The debubblizer comprises a first foamed body disposed closer to the blood inlet port, and a second foamed body disposed closer to the blood storage chamber, the first foamed body having a mesh number larger than the mesh number of the second foamed body.

The rib may include irregular surface portions transversely across the blood passage.

BEST MODE FOR CARRYING OUT THE INVENTION

Preferred embodiments of a blood reservoir according to the present invention will be described in detail with reference to the accompanying drawings.

Figure 1:
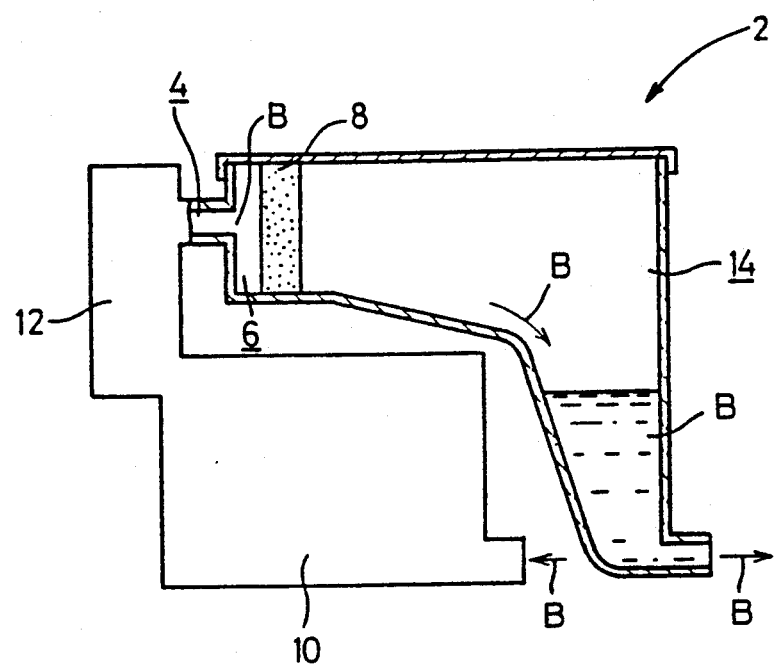
FIG. 1 is a schematic elevational view of a conventional blood reservoir.
Figure 2:
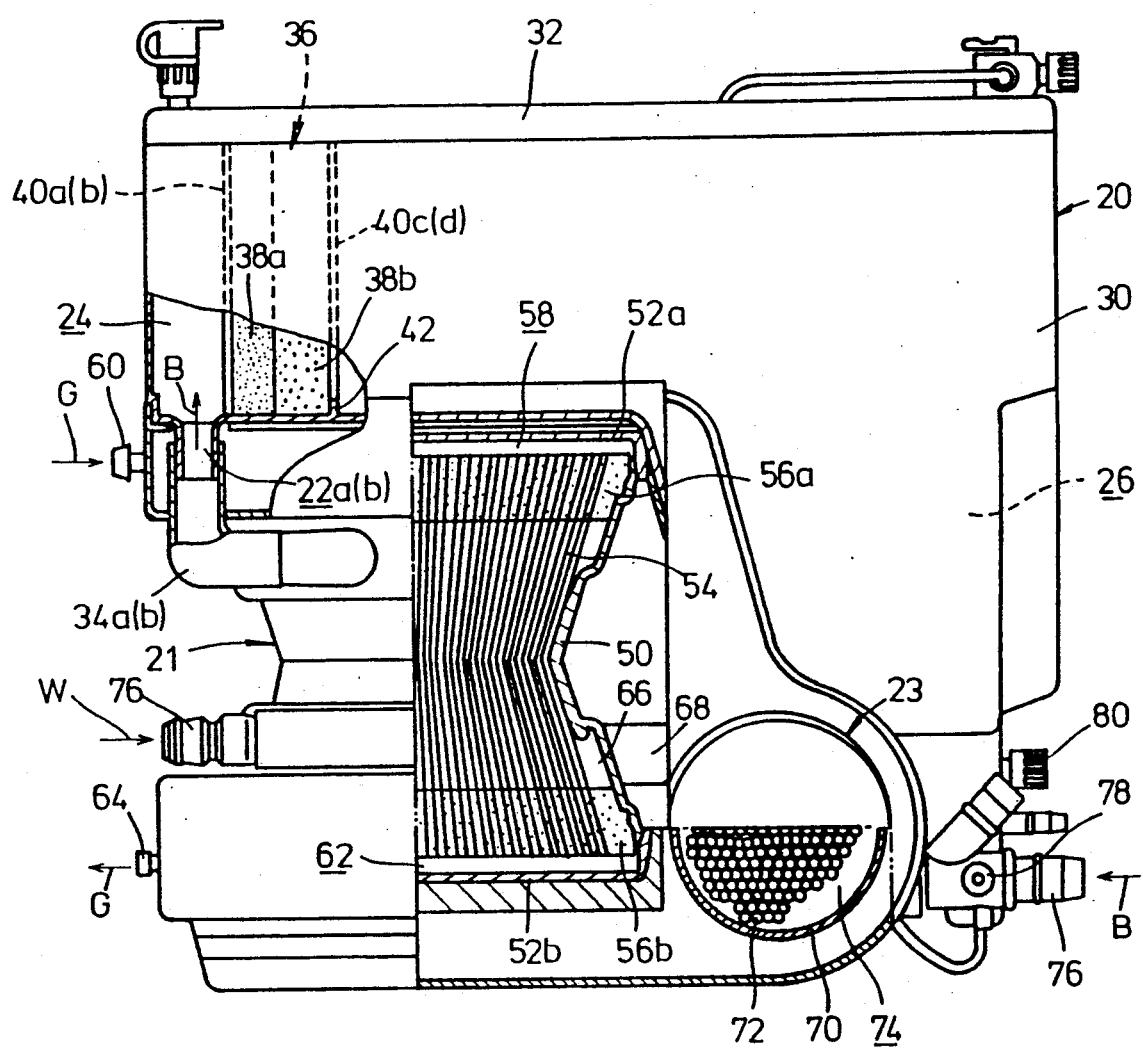
FIG. 2 is a side elevational view, partly in cross section, of an artificial lung apparatus incorporating a blood reservoir according to the present invention.

FIG. 2 shows a blood reservoir 20 according to the present invention which is combined with an artificial lung 21 for exchanging oxygen and carbon dioxide in blood B and a heat exchanger 28 for keeping the blood B at a predetermined temperature.

Figure 3:
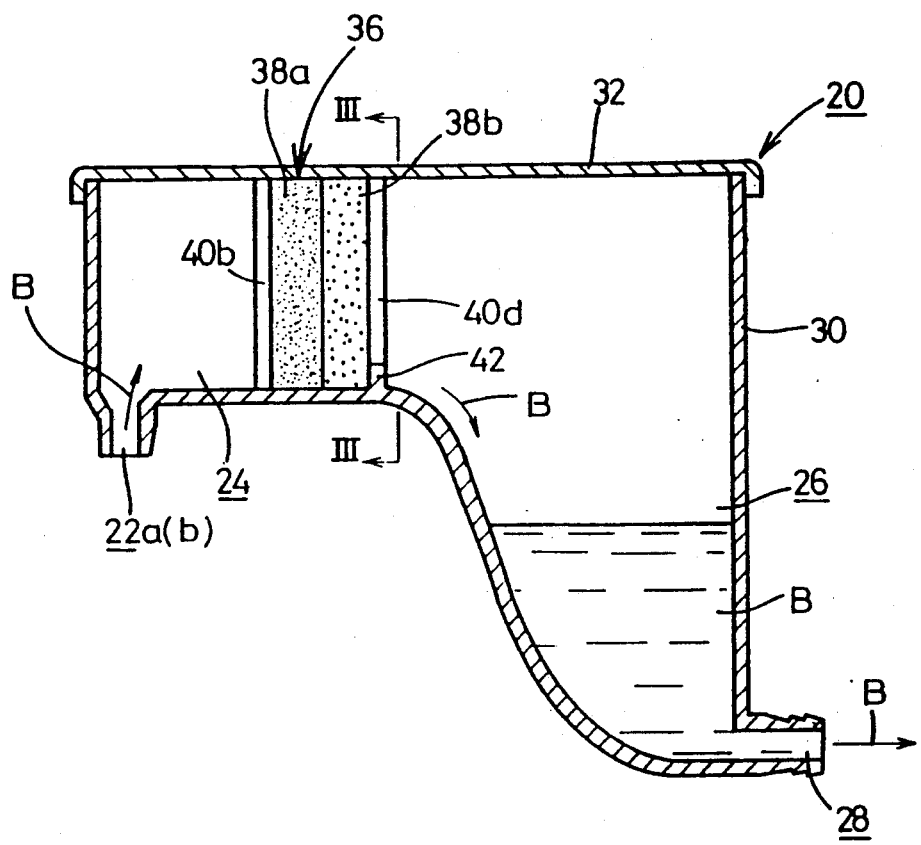
FIG. 3 is a vertical cross-sectional view of the blood reservoir of the invention.
Figure 4:
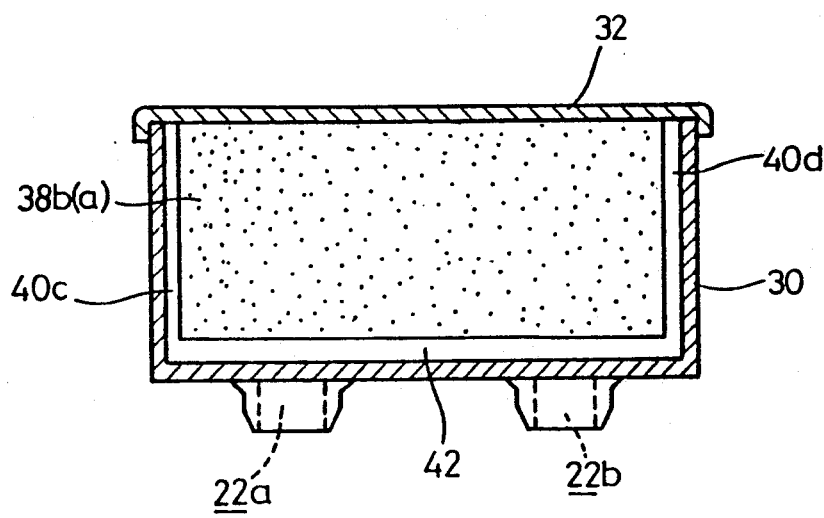
FIG. 4 is a cross-sectional view taken along line IV—IV of FIG. 3.

The blood reservoir 20 will first be described with reference to FIGS. 3 and 4.

The blood reservoir 20 is a blood reservoir of the hard shell type for use in an extra corporeal blood circulation circuit. As shown in FIG. 3, the blood reservoir 20 has a pair of blood inlet ports 22a, 22b, a blood inlet chamber 24 communicating with the blood inlet ports 22a, 22b and having a bottom which is substantially at the same level as the blood inlet ports 22a, 22b, a blood storage chamber 26 communicating with the blood inlet chamber 24 and having a bottom extending progressively downwardly from the blood inlet chamber 24, and a blood outlet port 28 defined in the lower end of the blood storage chamber 26. The blood reservoir 20 comprises a container housing 30 of a hard material such as hard polyvinyl chloride, polystyrene, polycarbonate, or the like. The container housing 30 has an upper opening closed by a cover 32. The container housing 30 should preferably be transparent so as to allow the user to visually observe the blood B stored in the container casing 2.

The blood inlet ports 22a, 22b are connected to blood outlet tubes 34a, 34b (see FIG. 2) from the artificial lung 21. The blood inlet chamber 24 communicating with the blood inlet ports 22a, 22b defines a blood passage extending from the blood inlet ports 22a, 22b to the blood storage chamber 26. The blood inlet chamber 24 is higher in position than the blood storage chamber 26, and has a bottom which is substantially at the same level as the blood inlet ports 22a, 22b, as described above. The bottom of the blood inlet chamber 24 may be flat or semicylindrical in shape. However, the flat bottom is preferable since a blood debubblizer (described later) can easily be placed thereon. The blood storage chamber 26 communicating with the blood inlet chamber 24 serves to store the blood B which has flowed into the blood reservoir 20. The bottom of the blood storage chamber 26 extends progressively downwardly from the blood inlet chamber 24. The blood B which is temporarily stored in the blood reservoir 20 is discharged out from the blood outlet port 28 defined in the lower end of the blood storage chamber 26.

The blood reservoir 20 also has a blood debubblizer 36 disposed in the housing 30 and extending transversely fully in and across the blood passage defined by the blood inlet chamber 24. The debubblizer 36 serves to remove air bubbles from the blood B which has flowed into the blood inlet chamber 24 so that the blood B free of air bubbles can be delivered into the blood storage chamber 26. The debubblizer 36 is generally in the form of of foamed bodies which are of a hydrophobic nature to allow air bubbles in the blood to grow and be removed. The foamed body is of a three-dimensional mesh structure. In the illustrated embodiment, the debubblizer 36 is composed of a foamed body 38a of a larger mesh number and a foamed body 38b of a smaller number mesh size, the foamed bodies 38a, 38b are arranged size by size. The foamed body 38a is positioned closer to the blood inlet ports 22a, 22b, whereas the foamed body 38b is positioned closer to the blood storage chamber 26. The mesh number referred to above represents the number of interstices or openings occurring per length of 25.4 mm (1 inch), and is originally an indication of the size of openings of a screen or sieve.

The debubblizer 36 is held in intimate contact with the bottom of the blood inlet chamber 24 and extends across the full width of the blood passage so that the incoming blood B will be in full contact with the debubblizer 36. The debubblizer 36 is also held in intimate contact with the side walls of the housing 30. The upper end of the debubblizer 36 is preferably held in intimate contact with the cover 32 mounted on the top of the housing 30 in order to prevent the debubblizer 36 from being moved by the blood flow or to prevent the blood B from flowing out beyond the upper end of the debubblizer 36. In order to prevent the debubblizer 36 from being moved, the housing 30 has four ridges 40a through 40d projecting from the inner side surfaces of the housing 30 on both lateral sides of the debubblizer 36 at the opposite surfaces thereof. The housing 30 also has a rib 42 projecting a certain height from the bottom of the blood inlet chamber 24. The rib 42 is disposed at the edge debubblizer 36 near the blood storage chamber 26, i.e., on the downstream side of the debubblizer 36 with respect to the blood flow, and extends the full width of the blood passage defined by the blood inlet chamber 24. The rib 42 is held in contact with the foamed body 38b.

The artificial lung 21 coupled to the blood reservoir 20 comprises a housing 50 and attachment covers 52a, 52b closing the upper and lower ends, respectively, of the housing 50. The housing 50 accommodates therein a number of hollow fiber membranes 54 which are vertically disposed in spaced relation to each other. The hollow fiber membranes 54 have opposite open ends held in the housing 50 by partitions 56a, 56b in a fluidtight manner, with the open ends remaining open. The attachment cover 52a, the housing 50, and the partition 56a jointly define a gas inlet space 58 communicating with the hollow spaces in the hollow fiber membranes 54 and connected to a gas inlet port 60. The other attachment cover 52b, the housing 50, and the partition 56b jointly define a gas outlet space 62 communicating with the hollow spaces in the hollow fiber membranes 54 and connected to a gas outlet port 64. The inner wall surface of the housing 50, the partitions 56a, 56b, and the outer wall surfaces of the hollow fiber membranes 54 jointly define a blood chamber 66 connected to a blood inlet tube 68 communicating with the heat exchanger 23 and the blood outlet tubes 34a, 34b which communicate with the blood reservoir 20.

The blood outlet tubes 34a, 34b of the artificial lung 21 are joined in a fluidtight manner to the blood inlet ports 22a, 22b of the blood reservoir 20. The blood outlet tubes 34a, 34b and the blood inlet ports 22a, 22b may be joined by threaded interfitting engagement, tapered interfitting engagement, fitting engagement through an O-ring, ultrasonic or high-frequency bonding, or adhesive bonding.

The artificial lung 21 is of the type which delivers a gas G containing oxygen such as air into the hollow fiber membranes 54 and allows the blood B to flow outside of the hollow fiber membranes 54 for a gaseous exchange between the gas G and the blood G. Alternatively, the artificial lung 21 may be of the type which delivers the blood B into the hollow fiber membranes 54 and the gas G containing oxygen around the hollow fiber membranes 54 for a gaseous exchange between the gas G and the blood B, or of the type which includes flat membranes for a gaseous exchange. Preferably, the artificial lung 21 should be of the type which passes the blood B around the hollow fiber membranes 54 as described above in this embodiment. With the artificial lung 21 of this type being employed, since any pressure loss across the artificial lung 21 is small, a blood circulation circuit incorporating the blood reservoir 20 is not required to have a blood delivery pump in front of the artificial lung 21, but the blood B can be fed by gravity from the patient to the artificial lung 21 and the blood reservoir 20.

The heat exchanger 23 is coupled to the blood inlet tube 68 of the artificial lung 21. The heat exchanger 23 has a number of heat exchanging tubes 72 disposed in a casing 70 in spaced relation to each other and extending in the longitudinal direction of the casing 70. The opposite open ends of the heat exchanging tubes 72 are held on side walls of the casing 70 by partitions (not shown) in a fluidtight manner, with the open ends of the tubes 72 remaining open. The partitions, the side walls of the casing 70, and the outer wall surfaces of the heat exchanging tubes 72 jointly define a space 74 which communicates with a blood inlet port 76 and the blood inlet tube 68 of the artificial lung 21. The inner spaces in the heat exchanging tubes 72, which are isolated from the space 74 in a fluidtight manner, communicate with a water inlet port 77 communicating with the exterior of one of the partitions of the casing 70 and a water outlet port (not shown) communicating with the exterior of the other partition of the casing 70. Warm or cold water W is supplied from the water inlet port 77 into the heat exchanging tubes 72, and warms or cools the blood B held in contact with the heat exchanging tubes 72. The heat exchanger 23 may be of the type in which the blood B is passed through the heat exchanging tubes 72 and a cooling or warming medium is passed around the heat exchanging tubes 72. The heat exchanger 23 and the blood reservoir 20 further have ports 78, 80, respectively, for the insertion of temperature sensor probes.

The blood reservoir of the above embodiment is basically constructed as described above. Operation and advantages of the blood reservoir will be described below.

The blood reservoir 20, the artificial lung 21, and the heat exchanger 23 which are combined together serve as an artificial lung apparatus. The blood B is introduced from the blood inlet port 76 into the casing 70 of the heat exchanger 23, and warmed or cooled by the water W flowing through the heat exchanging tubes 72 while the blood B is flowing toward the blood inlet tube 68 of the artificial lung 21.

Then, the blood B flows from the blood inlet tube 68 into the housing 50 of the artificial lung 21. During passage through the blood chamber 66, a gaseous exchange is effected between the blood B and the gas G containing oxygen which flows through the hollow fiber membranes 54, thereby removing excessive carbon dioxide from the blood B and adding oxygen to the blood B. The blood B to which oxygen is added flows out of the artificial lung 21 from the blood outlet tubes 34a, 34b and flows into the blood reservoir 20 through the blood inlet ports 22a, 22b. The blood B introduced from the blood inlet ports 22a, 22b now reaches the debubblizer 36 in the blood inlet chamber 24. Since the side of the debubblizer 36 closer to the blood storage chamber 26 is held against the rib 42 which extends the full width of the blood passage defined by the blood inlet chamber 24 and projects upwardly a certain distance from the bottom of the blood inlet chamber 24, the blood B is temporarily forced to stay and be deflected just in front of the rib 42 while in contact with the debubblizer 36. Accordingly, the blood B passes through the debubblizer 36 in a sufficient period of time and is kept in contact with the debubblizer 36 through a sufficient area or at a sufficient frequency. Therefore, air bubbles contained in the blood B contact the cells of the foamed bodies 38a, 38b of the debubblizer 36 and are combined into larger air bubbles, which are moved from the blood B into an upper space in the blood reservoir 20 and are reliably removed. Inasmuch as the two foamed bodies 38a, 38b have different mesh number which become smaller in the direction in which the blood B flows, the pressure loss across the debubblizer 36 is not increased, and the air bubbles in the blood B are brought into sufficient contact with the cells of the foamed bodies 38a, 38b, with the result that the blood B is effectively debubblized.

Figure 5:
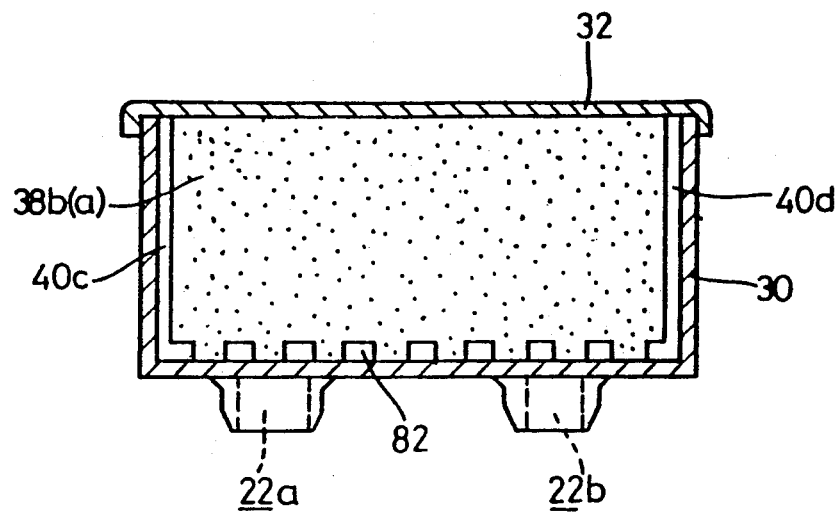
FIG. 5 is a cross-sectional view of a blood inlet chamber in a blood reservoir according to a comparative example.
Figure 6:
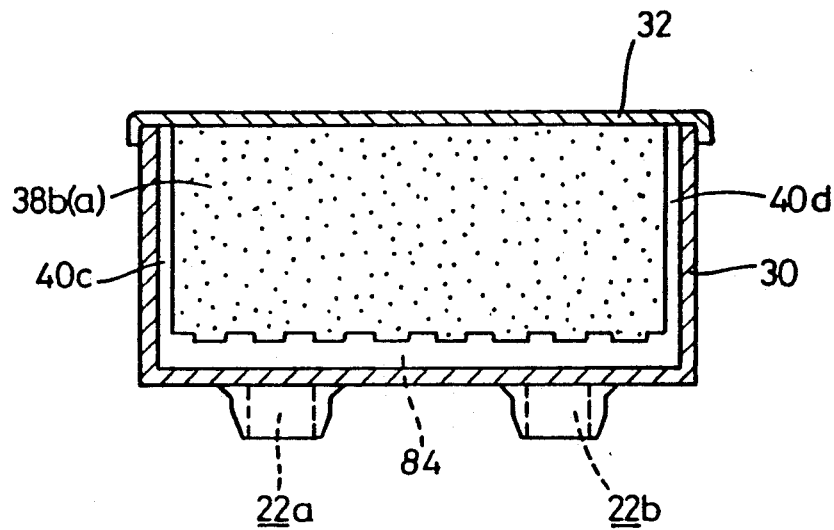
FIG. 6 is a cross-sectional view of a blood inlet chamber in a blood reservoir according to another embodiment of the present invention.

The rib 42 is required to extend the full transverse width of the blood passage defined by the blood inlet chamber 24. In this embodiment in which the blood inlet chamber 24 has a flat smooth bottom, as shown in FIG. 4, the rib 42 has to extend continuously up to the opposite lateral sides of the housing 30. More specifically, as shown in FIG. 5, if a rib 82 projecting from the bottom of the housing 50 is of a discontinuous shape and does not extend the entire transverse region of the blood passage defined by the blood inlet channel 24, the blood B flowing through the blood inlet chamber 24 passes through the recesses of the rib 82 when the blood B is to contact the debubblizer 36. Therefore, the rib 82 is not effective to keep the blood B in contact with the debubblizer 36. However, as shown in FIG. 6, providing a rib 84 extends the entire transverse region of the blood passage of the blood inlet chamber 24, the rib 84 is not required to be of a constant height, but may have irregular surface portions of different heights transversely across the blood passage, and yet can maintain the blood B in sufficient contact with the debubblizer 36. If the height of the rib 42 or 82 were less than 1 mm, it would not be able to force the blood B to stay or be deflected in contact with the debubblizer 36. If the height of the rib 42 or 82 were in excess of 50 mm, it would tend to keep the blood B excessively in the blood inlet chamber 24, thus increasing the priming volume of the blood reservoir 20. Therefore, the rib 42 or 82 should preferably be of a height ranging from 1 mm to 50 mm, more preferably ranging from 1 mm to 20 mm, and most preferably ranging from 2 mm to 10 mm. The rib 42 or 82 may be formed integrally with the housing 30 when the housing 30 is injection-molded, or may be separately formed and then bonded to the housing 30 by high-frequency fusion, thermal fusion, or adhesive bonding. At any rate, it is necessary that the rib 42 or 82 be held in intimate contact with the bottom in a fluidtight fashion in the blood passage of the blood inlet chamber 24.

The blood B from which air bubbles have been removed by the debubblizer 36 flows from the blood inlet chamber 24 into the blood storage chamber 26. After the blood B has temporarily been stored in the blood storage chamber 26, it is delivered to the patient's body from the blood outlet port 38 in the lower end of the blood storage chamber 26.

An experiment conducted on the blood reservoir of the present invention will be described below.

Figure 7:
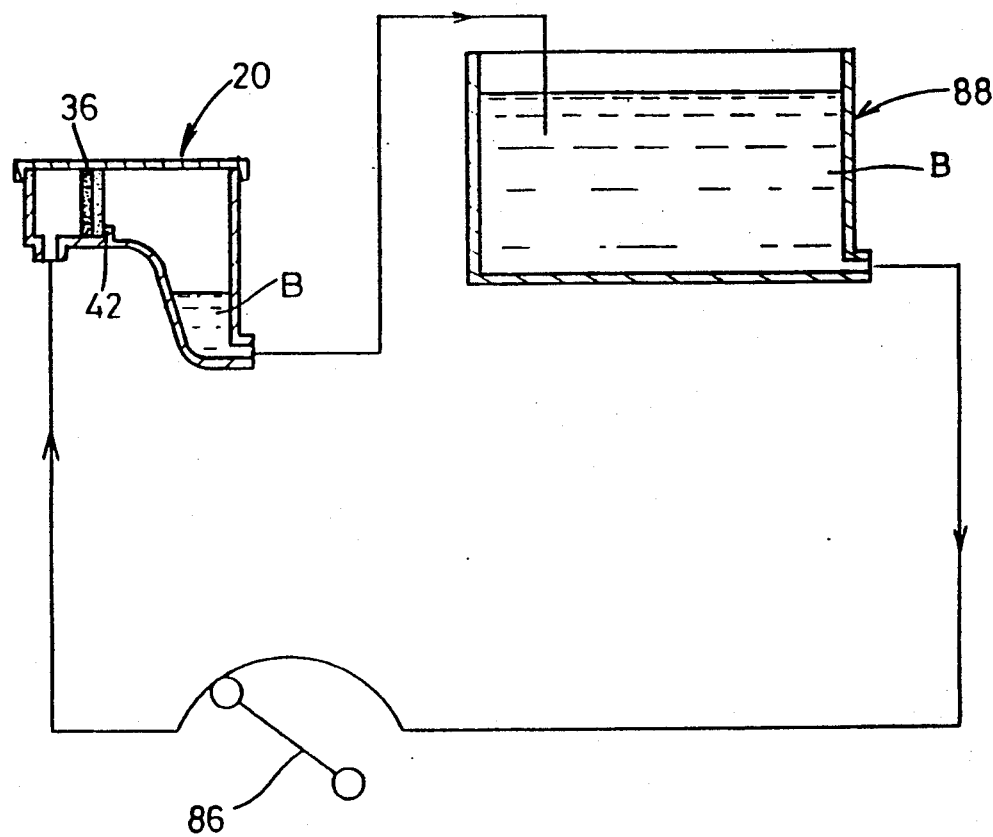
FIG. 7 is a diagram of a blood circuit employed in a blood circulation experiment conducted on the blood reservoir according to the present invention.

As shown in FIG. 7, there was employed a blood reservoir 20 having a storage capacity of 4 l and including a blood inlet chamber 24 having a length of 30 mm, a width of 160 mm, and a flat bottom. The blood passage extending from the blood inlet chamber 24 to the blood storage chamber 26 had a rib 42 extending across the blood passage fully in its transverse direction and projecting a height of 3 mm from the bottom of the blood inlet chamber 24. The blood reservoir 20 also had a debubblizer 36 held closely against the rib 42 and composed of a foamed body 38a (having a thickness of 15 mm) made of a polyurethane foam having a mesh number of 13, the foamed body 38a being positioned closer to the blood inlet ports 22a, 22b, and a foamed body 38b (having a thickness of 15 mm) made of a polyurethane foam having a mesh number of 8, the foamed body 38b being held closely against the foamed body 38a and positioned closer to the blood storage chamber 26. An experimental blood circuit was constructed of the blood reservoir 20 and a blood storage tank 88 having a storage capacity of 20 l and connected to the blood reservoir 20 by a roller pump 86. Using the experimental blood circuit, a blood circulation experiment was carried out at a blood flow rate of 4 l/min. to determine how air bubbles were mixed into the blood B in the blood storage chamber 26 of the blood reservoir 20.

A comparative blood circulation experiment was also conducted using the same blood reservoir as the blood reservoir 20 except that no projecting rib 42 was disposed on the bottom of the blood inlet chamber 24, and also using the same experimental blood circuit as described above, and it was determined how air bubbles were mixed into the blood in the blood storage chamber of the blood reservoir.

It was found as the results of the experiments that the debubblizer 34 in the blood reservoir 20 having the rib 42 was more effective in removing air bubbles from the blood than the debubblizer in the comparative blood reservoir having no rib 42. Substantially no air bubbles were found flowing into the blood storage chamber 26.

INDUSTRIAL APPLICABILITY

With the present invention, as described above, the blood reservoir has a blood inlet chamber having a bottom located at substantially the same level as blood inlet ports, a blood storage chamber positioned downwardly of the blood inlet chamber and having a blood outlet port, and a blood debubblizer disposed between the blood inlet chamber and the blood storage chamber and extending the full width across the blood passage defined by the blood inlet chamber. A rib is held against the side of the debubblizer closer to the blood storage chamber and extends the full width across the blood passage, the rib projecting from the bottom of the blood inlet chamber. When the blood introduced from the blood inlet ports into the blood storage container is brought into contact with the debubblizer in the blood inlet chamber, the blood is forced by the rib to temporarily stay in contact with the debubblizer and also to be deflected. Therefore, the blood remains in contact with the debubblizer over a long period of time, and the deflected blood flow causes the blood to be kept in contact with the debubblizer through an increased area or at an increased frequency. The blood is thus debubblized by the debubblizer so effectively that even small air bubbles can sufficiently be removed from the blood. Since the blood remains in sufficient contact with the debubblizer, the debubblizer does not develop an excessive pressure loss which would otherwise be brought about by an increased thickness of the debubblizer. Consequently, air bubbles can effectively be removed from the blood while at the same time maintaining a required amount of flood. As a result, it is possible to achieve safer extracorporeal circulation of blood when the blood reservoir is incorporated in an extracorporeal blood circulation circuit.

Although certain preferred embodiments have been shown and described, it should be understood that many changes and modifications may be made therein without departing from the scope of the appended claims.

I claim:

1. A blood reservoir comprising a blood inlet chamber having a blood inlet port, a blood storage chamber communicating with the blood inlet chamber and having a blood outlet port in a lower end which is positioned downwardly of said blood inlet chamber, and a blood debubblizer extending fully across a blood passage of said blood inlet chamber which leads to said blood storage chamber, comprising a rib held against the side of said debubblizer closer to said blood storage chamber and extending fully across said blood passage, said rib projecting a predetermined distance upwardly from the bottom of said blood inlet chamber.

2. A blood reservoir according to claim 1, wherein said rib has a height ranging from 1 mm to 50 mm.

3. A blood reservoir according to claim 1, wherein said debubblizer comprises a first foamed body disposed closer to said blood inlet port, and a second foamed body disposed closer to said blood storage chamber, said first foamed body having a mesh number larger than the mesh number of said second foamed body.

4. A blood reservoir according to claim 1, wherein said rib includes surface portions having different heights, each of said surface portions being disposed transversely across a portion of the blood passage.

* * * * *